(12) United States Patent
Richards

(10) Patent No.: US 9,356,305 B2
(45) Date of Patent: May 31, 2016

(54) FUEL CELLS

(75) Inventor: Robert W. Richards, Tredegar (GB)

(73) Assignee: LION LABORATORIES LIMITED, Barry, Glamorgan (GB)

(*) Notice: Subject to any disclaimer, the term of this patent is extended or adjusted under 35 U.S.C. 154(b) by 1382 days.

(21) Appl. No.: 12/519,222

(22) PCT Filed: Nov. 5, 2007

(86) PCT No.: PCT/GB2007/004214
§ 371 (c)(1),
(2), (4) Date: Jun. 15, 2009

(87) PCT Pub. No.: WO2008/071900
PCT Pub. Date: Jun. 19, 2008

(65) Prior Publication Data
US 2010/0028753 A1    Feb. 4, 2010

Related U.S. Application Data

(60) Provisional application No. 60/885,475, filed on Jan. 18, 2007.

(30) Foreign Application Priority Data

Dec. 15, 2006 (GB) .................................. 0625028.6

(51) Int. Cl.
*H01M 8/02* (2006.01)
*H01M 8/08* (2006.01)
*H01M 8/10* (2016.01)
(Continued)

(52) U.S. Cl.
CPC ................ *H01M 8/08* (2013.01); *H01M 8/023* (2013.01); *H01M 8/0232* (2013.01); *H01M 8/0245* (2013.01); *H01M 8/1013* (2013.01);
(Continued)

(58) Field of Classification Search
CPC ........ Y02E 60/50; H01M 8/002; H01M 8/08; H01M 8/0258
USPC ............................................ 429/456; 73/23.3
See application file for complete search history.

(56) References Cited

U.S. PATENT DOCUMENTS 3,966,579 A * 6/1976 Chang ................ G01N 27/4045
204/406
4,171,253 A * 10/1979 Nolan ................ G01N 27/4045
204/406

(Continued)

FOREIGN PATENT DOCUMENTS

CA    2410005 A1    12/2001
CA    2608013 A1    11/2006
(Continued)

*Primary Examiner* — Ula C Ruddock
*Assistant Examiner* — Archer Dudley
(74) *Attorney, Agent, or Firm* — King & Schickli, PLLC

(57) ABSTRACT

This invention relates to fuel cells. A fuel cell 10 defines a space 11 having an air/ethanol inlet 12 and an outlet source 13. The operative part of the fuel cell, 14, includes a pvc substrate 15, a working electrode 16 and a counter electrode 17. A working electrode current collector 20 extends over the working electrode 16, whilst a counter electrode current collector 21 extends across the counter electrode 17. The electrodes formed from tantalum. At least one of the current collector electrodes 20, 21 are non-conformably depressed into their associated electrode to define a channel for containing electrolyte whereby charge can be transferred to the current collector by ionic exchange.

20 Claims, 2 Drawing Sheets

(51) Int. Cl.
  *G01N 33/497* (2006.01)
  *H01M 8/06* (2016.01)

(52) U.S. Cl.
  CPC ......... *G01N33/4972* (2013.01); *H01M 8/0258* (2013.01); *H01M 8/0637* (2013.01); *Y02E 60/522* (2013.01)

(56) References Cited

U.S. PATENT DOCUMENTS

| | | | | |
|---|---|---|---|---|
| 4,929,517 | A * | 5/1990 | Luoma | C04B 37/008 429/509 |
| 6,200,459 | B1 * | 3/2001 | Vadgama | G01N 27/40 204/415 |
| 6,815,105 | B2 * | 11/2004 | Cooper | H01M 2/1653 204/243.1 |
| 2004/0081878 | A1 * | 4/2004 | Mardilovich | H01M 8/0228 429/456 |
| 2005/0058875 | A1 | 3/2005 | Jerome | |
| 2006/0216570 | A1 * | 9/2006 | Vyas | H01M 8/0204 429/457 |
| 2007/0154765 | A1 * | 7/2007 | Bayer | G01N 33/4972 429/506 |

FOREIGN PATENT DOCUMENTS

| | | | |
|---|---|---|---|
| EP | 0 652 436 | 5/1995 | |
| JP | 60 053837 | 3/1985 | |
| WO | WO2005029619 | * 3/2005 | ............. H01M 8/00 |

* cited by examiner

FUEL CELLS

This application claims the benefit of U.S. Provisional Patent Application Ser. No. 60/885,475, the disclosure of which is incorporated herein by reference.

This invention relates to fuel cells and, in particular, but not exclusively to fuel cells suitable for detecting the presence of alcohol in a breath sample.

FIELD OF THE INVENTION

The typical fuel cell used in breath alcohol testing includes a housing having a gas inlet and outlet to allow a breath/ethanol sample to flow through a chamber, one wall of which is formed by a working electrode. The working electrode, typically platinum black, is usually deposited on a PVC substrate, which has a counter electrode on its opposed face. For manufacturing convenience the PVC substrate is often formed in two halves and then the two non-electrode surfaces are abutted. The PVC and electrodes contain sulphuric acid electrolyte.

BACKGROUND OF THE INVENTION

The operation of such electrodes is well known in the art, but basically electron flow is generated due to the chemical reaction between the ethanol and the working electrode and oxygen and the counter electrode.

This current is collected by current collectors which are engaged on the surface of the respective electrodes. Typically these electrodes are in the form of a loop. In one design approach the loop is formed from platinum; rhodium alloy. Platinum is chosen because it is reasonably inert to sulphuric acid, but it is over brittle for its purpose and is therefore alloyed to reduce this problem. The resultant material is relatively malleable, but is expensive and there can be problems resulting from bi-metallic behaviour. The alternative approach is to coat a stainless steel loop with gold. In practice this means there needs to be a nickel intermediate layer, because gold will not adhere properly to stainless steel. This gives a degree of rigidity and is thought to give better contact between the electrode and the current collector, but in practise there are problems with this approach, because the deposited gold often has minute holes in it. The nickel then becomes eaten away by the sulphuric acid electrolyte and in bad cases can allow the electrolyte to flow along the gap left by the nickel out through the housing and into the electronics of the associated device.

In any event the fuel cells do not reach a steady state for some considerable period after manufacture and there are still concerns about the contact between the current collector and the electrode.

A recent proposal, in connection with platinum wire, is to try to press the wire more firmly against the electrode by means of formations on the housing. This causes localised deformation in the platinum wire and any improvement in contact only takes place locally.

One or more of these problems is addressed by various aspects of the Applicants invention.

SUMMARY OF THE INVENTION

Thus from a first aspect the invention consists in a fuel cell having a housing, a substrate in the housing for containing electrolyte and having a working electrode and a counter electrode formed on respective opposed surfaces; and a current collector for each electrode characterised in that at least one current collector is non-conformably depressed into its associated electrode to define a channel for containing electrolyte whereby charge can be transferred to the current collector by ionic conduction.

The Applicants have appreciated that, contrary to current prejudice in the art, what is important is not the direct physical contact between the current collector and the electrode, but rather a good film of electrolyte between the current collector and electrode, because the efficient mechanism for electron transfer is by ionic conduction. By having the depression take place non-conformably, a channel can be created substantially along the length of the current collector and not simply where pressure is applied.

Conveniently the housing includes a lid having formations on its underside for engaging a current collector for depressing the current collector into the substrate, where the lid is in a closed position. Typically the lid will overlie the working electrode. Additionally, or alternatively, the housing may have a base having formations on its upper side for engaging a current collector for depressing the current collector into the substrate. Conveniently the counter electrode will overlie the base.

The formations associated with the working electrode current collector may define a labyrinth path for a gas sample to spread the sample over the working electrode.

The counter electrode may face a chamber of sufficient dimension to contain free oxygen. This should accelerate the reactive time of the counter electrode.

In any of the above embodiments the current collectors may be tantalum and preferably the tantalum will be at least 95% pure. Tantalum is advantageous because it has a suitable resistivity, is extremely inert, is much cheaper than platinum, is much stiffer than platinum or its alloys allowing non-conformal depression of the electrode and it does not need to be used in an alloyed form. Conveniently the tantalum is covered with an oxide coating on at least part of the current collector. Typically this may be $Ta_2O_5$.

It any of the above arrangements the current collectors may pass through the housing and have a relatively rough surface adjacent the housing and the sale may further include seals deposited on the rough surface to prevent the flow of electrolyte from the housing. The rough surface may be provided by the oxide coating. The improved keying that will take place between the seal, which can conveniently be formed from adhesive, and the rough surface reduces the risk of seal failure.

From another aspect the invention consists in a fuel cell having at least one tantalum current collector.

In that case the fuel cell may include a housing and the/each current collector may pass through the housing and have a relatively rough surface adjacent the housing and further include a seal deposited on that rough surface. In this case the rough surface may be formed by $Ta_2O_5$ or other oxide coating.

From a still further aspect the invention consists in a fuel cell having a housing, a substrate in the housing for containing electrolyte and having a working electrode and a counter electrode formed on respective post surfaces wherein the housing has one or more formations for engaging on one of the electrodes to form a reservoir or reservoirs that contain excess electrolyte expressed from the substrate.

This approach overcomes a further problem with current devices where electrolyte expressed from the PVC substrate, due to temperature or pressure changes or the like, can coat the surface of the working electrode in a manner which reduces the rate of reaction between the ethanol or working gas and the working electrode.

From a still further aspect the invention consists in a fuel cell having a housing; a substrate in the housing for containing electrolyte and having a working electrode and a counter electrode formed on exposed surfaces; and a current collector for each electrode wherein there is a channel in each electrode for receiving a current collector and containing a film with electrolyte between the respective current collector and the electrode.

In any of the above arrangements containing a current collector, the current collector may be formed as a wire stub. This is particularly true when there is an electrolyte channel, because the need to increase the surface of contact may no longer exist.

It will be appreciated that such an arrangement not only saves in materials costs, but also in manufacturing costs.

The invention also consists in alcohol breath testing apparatus including the fuel cell as defined above.

Although the invention has been defined above, it is to be understood that it includes any inventive combination of the features set out above or in the following description.

BRIEF DESCRIPTION OF THE DRAWING FIGURES

The invention may be performed in various ways and a specific embodiment will now be described, by way of example, with reference to the accompanying drawings, in which.

BRIEF DESCRIPTION OF THE DRAWING FIGURES

Figure 1:
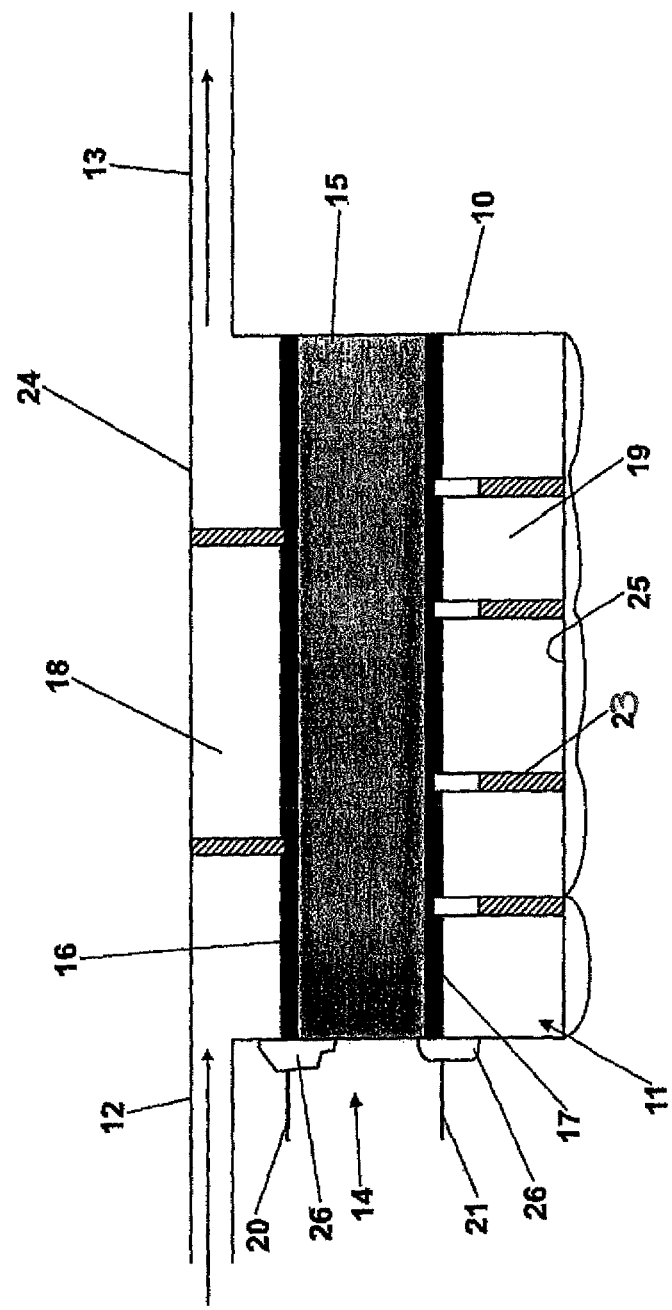
FIG. 1 is a schematic vertical section through a fuel cell.

Referring to FIG. 1 a fuel cell has a housing 10 defining a space 11 and having an air/ethanol inlet 12 and an outlet or exhaust 13. Suitable sampling mechanisms for passing air/ethanol or other working gas, through such fuel cells are well known in the art. Located within the space is the operative part of the fuel cell, which is generally indicated at 14. This comprises a PVC substrate 15, which bridges the space 11, and has a working electrode 16 and a counter electrode 17 on opposed surfaces. The working electrode 16 forms one wall of the working electrode chamber 18 that lies between the inlet 12 and outlet 13, whereas the counter electrode 17 overlies a counter electrode chamber 19. A working electrode current collector 20 extends over the working electrode 16, whilst a counter electrode current collector 21 extends across the counter electrode 17.

For convenience the substrate 15 may actually be in two halves, because it is then easier to deposit the platinum black which forms the electrodes on the surface of each half and then to abut the uncoated faces of the substrate elements together as shown in FIG. 1. The substrate 15 and the electrodes 16 and 17 contain sulphuric acid electrolyte.

With the exception of the size of the chamber 19 and the shape of the current collectors 20, 21, the design of the fuel cell described above is substantially that known in the art and its operation is well understood.

In addition to the above features the Applicant's have introduced the following inventive features:
1. The current collectors 20, 21 are formed from tantalum. This is inert to sulphuric, phosphoric or any other mineral acid, and to any alkali, both aqueous and non-aqueous. In addition material is inert to fused electrolyte media, which find application in high temperature fuel cells. In particular the material shows zero reaction to all concentrations of aqueous sulphuric acid.

Since the material is so resistant to corrosion, it does not create corrosion potentials, which so plague the prior art devices and create extraneous noise.

Tantalum has an acceptable resistivity and the Applicants have established that it is less prone to Johnson Nqvist noise and Peltier Seebeck effects, which also contribute to fuel cell sensor background instability. The material is considerably cheaper than the materials which are currently used and currently are indeed of the order of 10% of the cost of the platinum wire. Tantalum is also much harder than the platinum wire and has greater tensile strength.

In more detail the use of tantalum provides the additional benefits as a current collector for a fuel cell.
Additional Advantages of Using Tantalum as a Fuel Cell Sensor Current Collectors.

Ideally, all fuel sensors would have an ambient background emf of zero volts.

In practice this is not the case because, in part, cells internally generate transient, variable background potentials of the order of tens of µV.

It is important to emphasise that the "rest potentials" referred to here do not result from reduction or oxidation of gaseous reagents from the environment and are not of external origin.

It is contended that internally generated background potentials can be reduced by employing Ta as a current collector material because it eliminates or reduces contributions from the following effects:
Electrochemical Effect Arising from Compositional Differences between Current Collector Couples.

Compositional differences in composite current collector materials can generate electrochemical potentials between cell collector couples.

For example, consider Pt-10% Rh, a material routinely used as a current collector because of its superior mechanical properties to those of pure Pt.

Unless the alloy is perfectly homogeneous it is possible that electrochemical potentials (of the order of µV) can be generated on the surface of the collector (i.e. between relative anodic and cathodic areas).

In this circumstance, a measurable emf can result from a difference in potentials between two collectors in a cell.

Such a potential is not expected from collectors constructed of a single pure material where compositional variations are less likely.
Electrochemical Effect Arising from Hydrogen Absorption and Adsorption.

Platinum and platinum rhodium alloys have an enormous capacity to absorb and adsorp hydrogen gas. The effect is rapid even at room temperature when the metal is in contact with hydrogen gas in an acid medium.

The process is usually interpreted as involving the metal interaction with nascent hydrogen present in the following (idealised) equilibrium:

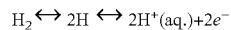

Experiments at Lion Laboratories have conclusively demonstrated that Pt and Pt-10% Rh wire current collectors absorb\adsorp significant quantities of hydrogen under certain conditions which is then desorbed over extended periods.

The desorption process generates a large, variable (diminishing) potential on the current collector.

Differences in these potentials, between current collector couples, in turn, generate variable fuel cell background emfs.

It is contended that the problem is eliminated or reduced by using Ta as a current collector because of its much smaller tendency to absorb\adsorp hydrogen.

Seebeck-Peltier Effect.

The Seebeck effect generates sizeable potentials from small temperature differences across junctions of dissimilar metals.

The effect is especially significant across Pt/Pt-10% Rh junctions.

This is the combination employed in constructing S-type thermocouples and is, of course, the junction present when a Pt-10% Rh collector is used in contact with a Pt black electrode in a fuel cell sensor.

It is contended that the Seebeck effect is less significant in a Pt/Ta junction.

Temperature differences between a fuel cell current collector pair can be envisaged as generated in a number of ways e.g. by differential heat absorption from adjacent electronic components by Joule-Thompson cooling of the working electrode surface when breath samples are admitted to the fuel cell sensor heat changes accompanying reaction.

2. The greater resistance to bending of tantalum enables the possibility of it being non-conformably depressed into the surface of the respective electrode to form a channel 40 in the electrode 16 which will contain electrolyte 22 over a considerable surface of the current collector 20 allowing for effective ionic conduction. It will be understood that the current arrangement with platinum wire substantially only allows a line contact between the wire and the electrode.

Figure 2:
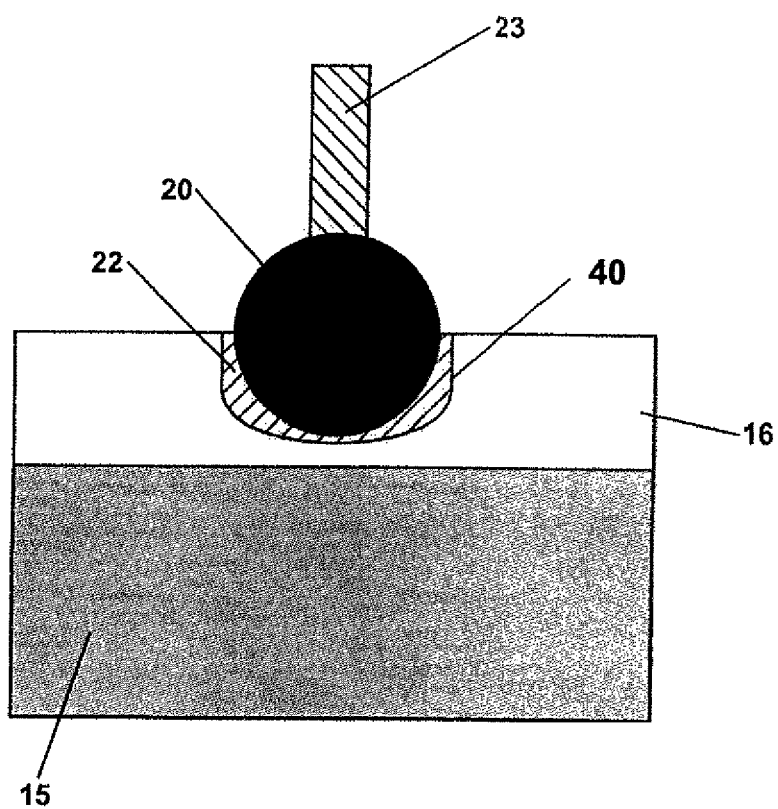
FIG. 2 is a schematic transversal cross-section of a part of the fuel cell of FIG. 1 showing the interface between an electrode and a current collector.

As can be seen in FIG. 2 and in FIG. 1 this non-conformal depression of the electrode 20 is achieved by ribs or plinths 23 formed on the lid 24 of the housing 10. The lid is preferably snap fitted on the rest of the housing 10 so that it physically pushes the current collector 20 down into the electrode 16.

Although FIG. 2 shows effectively displacement of the platinum black material of the electrode 16, it will be appreciated that a similar channel would be formed simply by compression of the underlying PVC material.

Similar plinths 23 can be provided on the base 25 to effect the same contact between the counter electrode 17 and the counter electrode current collector 21.

3. The plinths 23 or other formations, may form a labyrinth path between the inlet 12 and the outlet 13 so that the working gas travels across substantially all of the surface area of the working electrode to enhance the chemical reaction between the working gas and the electrode. 4. The plinths 23 or other formations may also act to contain locally electrolyte which is expressed from the substrate 15 due to temperature and/or pressure cycle or changes in humidity.

This stops the whole surface of the electrode becoming covered in electrolyte, which may inhibit the reactive process. The plinths 23 may have a similar effect to prevent "sloshing" of the electrolyte which has escaped from the substrate 15.

5. The chamber 19 is substantially oversize compared with current designs in order to allow a source of free oxygen to accelerate the reaction process at the counter electrode. It will be appreciated that in fact the base could be the lid and vice versa without any substantive change to the design.

6. The improved ionic contact between the current collectors and the electrodes means that it is no longer, in many instances at least, necessary to have a complete loop of the current collector. A simple stub of wire will suffice. This reduces both manufacturing costs and assembly costs.

7. The current collectors are preferably covered in an oxide such as tantalum pentoxide. This has a rough surface and significantly improves the keying between seals 26 and their respective current collectors 20, 21. This further reduces the likelihood of any electrolyte egress. Seals are conveniently formed from blobs of adhesive. Although wire stubs are sufficient to produce the required electrical effect, problems have been observed in assembly of some fuel cells due to rocking of the electrodes, creating damage adjacent the seals. It may therefore be desirable to form the current collectors 20, 21 into serpentine or other structures, in order to reduce the propensity for rocking, although often the provision of the plinths 23 will suffice.

The invention claimed is:

1. A fuel cell having:
   a housing;
   a substrate in the housing for containing an electrolyte and having a working electrode and a counter electrode formed on respective opposed surfaces;
   a current collector for each electrode; and
   at least one formation configured to partially submerge one of the current collectors into one of the electrodes, thereby defining a channel for containing the electrolyte whereby charge can be transferred to the one current collector by ionic conduction.

2. A fuel cell as claimed in claim 1 wherein the housing includes a lid, and wherein the at least one formation is associated with an underside of the lid for engaging one of the current collectors and for depressing the one current collector into the substrate, when the lid is in a closed position.

3. A fuel cell as claimed in claim 1 including a base having the at least one formation on an upper side for engaging one of the current collectors and for depressing one the current collector into the substrate.

4. A fuel cell as claimed in claim 2 including a plurality of formations, and wherein the plurality of formations associated with the working electrode current collector define a labyrinth path for a gas sample to spread the sample over the working electrode.

5. A fuel cell as claimed in claim 3 wherein the at least one formation associated with the working electrode current collector define a labyrinth path for a gas sample to spread the sample over the working electrode.

6. A fuel cell as claimed in claim 1 wherein the counter electrode faces a chamber of sufficient dimension to contain free oxygen.

7. A fuel cell as claimed in claim 1 wherein the current collectors are tantalum.

8. A fuel cell as claimed in claim 7 wherein the tantalum is at least 95 % pure.

9. A fuel cell as claimed in claim 8 wherein the tantalum is covered with an oxide coating on at least part of the current collectors.

10. A fuel cell as claimed in claim 9 wherein the oxide coating is $Ta_2O_5$.

11. A fuel cell as claimed in claim 1 wherein the current collectors pass through the housing and have a textured surface adjacent the housing and further including seals deposited on the textured surface to prevent the flow of the electrolyte from the housing.

12. A fuel cell as claimed in claim 11 wherein the textured surface is formed by a $Ta_2O_5$ or other oxide coating.

13. A fuel cell having:
   a housing,
   a substrate in the housing for containing electrolyte and having a working electrode and a counter electrode formed on respective opposed surfaces; and at least one current collector associated with each electrode;

wherein the housing has one or more formations for engaging at least one of the current collectors on one of the electrodes to form a reservoir or reservoirs, said reservoir or reservoirs partially containing the at least one of the current collectors and configured to contain the electrolyte excess expressed from the substrate.

14. A fuel cell having:

a housing including at least one formation;

a substrate in the housing for containing electrolyte and having a working electrode and a counter electrode formed on exposed surfaces; and a current collector for each electrode;

wherein the at least one formation is configured to form a channel in each electrode for both partially receiving one of the current collectors and containing a film of the electrolyte between the associated current collector and electrode.

15. A fuel cell as claimed in claim 1 wherein at least one of the current collectors is in the form of a wire stub.

16. A fuel cell as claimed in claim 14 wherein at least one of the current collectors is in the form of a wire stub.

17. An alcohol breath testing apparatus including a fuel cell as defined in claim 1.

18. The fuel cell as claimed in claim 1, wherein the one current collector remains at least partially outside the channel.

19. The fuel cell as claimed in claim 13, wherein the at least one of the current collectors remains at least partially outside the reservoir.

20. The fuel cell as claimed in claim 14, wherein the one of the current collectors remains at least partially outside the channel.

* * * * *